United States Patent [19]
Aramata et al.

[11] Patent Number: 5,720,731
[45] Date of Patent: Feb. 24, 1998

[54] PREFILLED SYRINGE FOR INJECTION OF TWO LIQUIDS

[75] Inventors: Masafumi Aramata, Neyagawa; Hitoshi Futagawa; Hideki Yagi, both of Kusatsu, all of Japan

[73] Assignee: Nissho Corporation, Osaka-fu, Japan

[21] Appl. No.: 630,989

[22] Filed: Apr. 12, 1996

[30] Foreign Application Priority Data

Apr. 12, 1995 [JP] Japan .................... 7-086781

[51] Int. Cl.⁶ .................................................. A61M 5/00
[52] U.S. Cl. ......................... 604/191; 604/218; 604/90
[58] Field of Search ......................... 604/218, 187, 604/191, 82–85, 89, 90

[56] References Cited

FOREIGN PATENT DOCUMENTS

| | | |
|---|---|---|
| 0072058 | 2/1983 | European Pat. Off. |
| 0245895 | 11/1987 | European Pat. Off. |
| 0520618 | 12/1992 | European Pat. Off. |
| 0568321 | 11/1993 | European Pat. Off. |

OTHER PUBLICATIONS

Database WPI, Section Ch, Week 9612, Derwent Publication Ltd., London, GB; Class B0-7, AN 96-110596 XP002012862 & JP-A-08 010 325 (Daikyo Gum Seiko KK), 16 Jan. 1996 (abstract).

*Primary Examiner*—John D. Yasko
*Attorney, Agent, or Firm*—Birch, Stewart, Kolasch & Birch, LLP

[57] ABSTRACT

Prefilled syringe for injection of two liquids includes a syringe body with an injection port at a closed end thereof, first and second gaskets fluid-tightly fitted into the syringe body to separate two medical solutions filled therein, and a closing member for closing the injection port. The syringe body is provided with bypassing grooves extending in the longitudinal direction of the syringe from a position adjacent to the closed end thereof. Liquid communication means is provided between the closed end and the first gasket. By pushing a plunger, the first and second gaskets are forced to move forward so that two medical solutions are injected one after another.

6 Claims, 4 Drawing Sheets

PREFILLED SYRINGE FOR INJECTION OF TWO LIQUIDS

BACKGROUND OF THE INVENTION

1. Field of the Invention

The present invention relates to a prefilled syringe for injection of two liquids and, more particularly, to a syringe previously filled with a dose of two medical solutions, especially, an anesthetic and a high viscous medical solution, separate from each other and adapted to be injected one after another.

2. Description of the Prior Art

A prefilled syringe is generally composed of a hollow tube closed at one end by a cap fitted thereon and a plunger inserted therein through the opposite open end so as to form a closed chamber into which a dose of a medical solution has been previously charged. In use, the medical solution can be injected by removing the cap from the tip and then fitting a hypodermic needle on the tip. Thus, the prefilled syringe is very easy to handle and can be sanitarily maintained before use. For these reasons, recently, prefilled syringes have been widely used.

On the other hand, if a medicine is a liquid with a high viscosity, it is required to use a thick needle to facilitate the injection. In addition, it is generally required to inject a large dose of such a high viscous medical solution into the body of a patient. Consequently, the patient is obliged to stand a great pain. To relieve the patient from such a pain, it is general practice to inject an anesthetic under the skin by means of a syringe before injecting such a high viscous medical solution into the site of the patient to be treated. In this case, the anesthetic is sucked into a separate syringe through a hypodermic needle and then injected under the skin of the patient to relieve the patient from the pain.

To reduce these problems, there has been proposed, in Japanese Utility model unexamined publication No. 6-66692, a prefilled syringe into which a medicine such as an anesthetic, a medical solution, a solvent, etc., can be properly sucked. This prefilled syringe is provided, on the barrel portion between the front and rear ends of the plunger arranged in place within the syringe, with a mark which indicates a limit of extraction of the plunger when sucking the medicine through the needle.

In the above prefilled syringe, however, the medicine or anesthetic is mixed with the other medical solution previously filled in the syringe. Mixing of the anesthetic with the other medical solution results in decrease of narcotic influence.

SUMMARY OF THE INVENTION

It is therefore an object of the present invention to provide a prefilled syringe for injection of two liquids, suitable for injection of two kinds of medicines including an anesthetic, without decreasing narcotic influence of the anesthetic.

According to the present invention the above object is solved by providing a prefilled syringe for injection of two liquids, including:

a syringe body composed of a hollow tube having a closed end and a proximal open end, said closed end being provided with an injection port for injection of medicine;

first and second gaskets which fluid-tightly fit into said syringe body; and a closing member for closing said injection port; characterized in that said syringe body is provided with one or more bypass grooves extending in the longitudinal direction of the syringe from a position adjacent to the closed end by a distance longer than the thickness of the first gasket, and that prefilled syringe has liquid communication means for retaining a channel or passage for liquid between an inner surface of said closed end and the first gasket to make a liquid communication between said bypass and injection port when said first gasket is brought into contact with the closed end of the syringe body.

The liquid communication means for retaining a channel or passage for liquid may be constituted by providing one or more projections or grooves on or in the inner wall of the closed end, or by providing one or more projections on or in the front wall of the first gasket.

According to the prefilled syringe thus constructed, the injection can be carried out easily by removing the closing member from the injection port of the prefilled syringe, fitting a hypodermic needle on the injection port, and then pushing a plunger with the finger.

Here, a process of injection will be explained briefly, making reference to FIGS. 2 and 3 of the accompanying drawings. FIG. 2 shows a prefilled syringe of the present invention before use. By pushing the plunger 2, the first and second gaskets 3, 4 are forced to move forward by sliding so that a first medical solution (e.g., an anesthetic) in the first chamber 13 is pushed out through the needle. All the first medical solution in the chamber 13 is pushed out when the first gasket is brought into contact with the inner wall of the closed end as shown in FIG. 3. At the same time, the second chamber 14 is communicated with the injection port through the bypass or groove 16 and the liquid communication means 6. By further pushing the plunger, the second fluid in the second chamber 14 is pushed out through the bypass 16, liquid communication means 6 and the needle 7.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Figure 1:
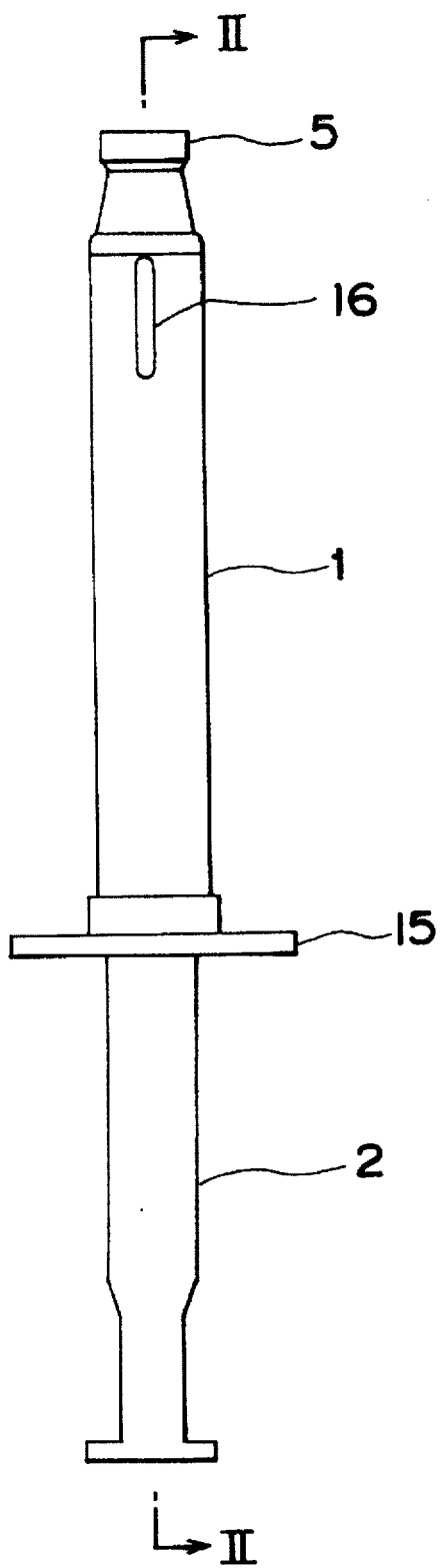
FIG. 1 is a plan view of a prefilled syringe according to the present invention.
Figure 2:
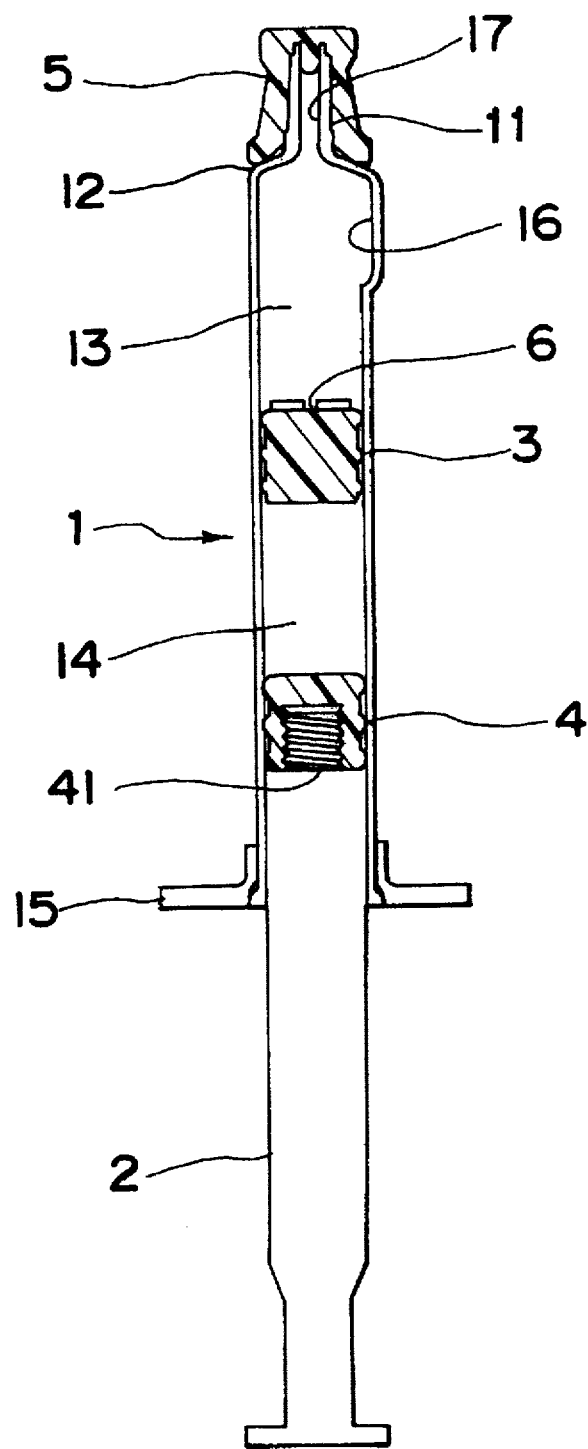
FIG. 2 is a cross-sectional view of the prefilled syringe, taken along the line X—X in FIG. 1.
Figure 3:
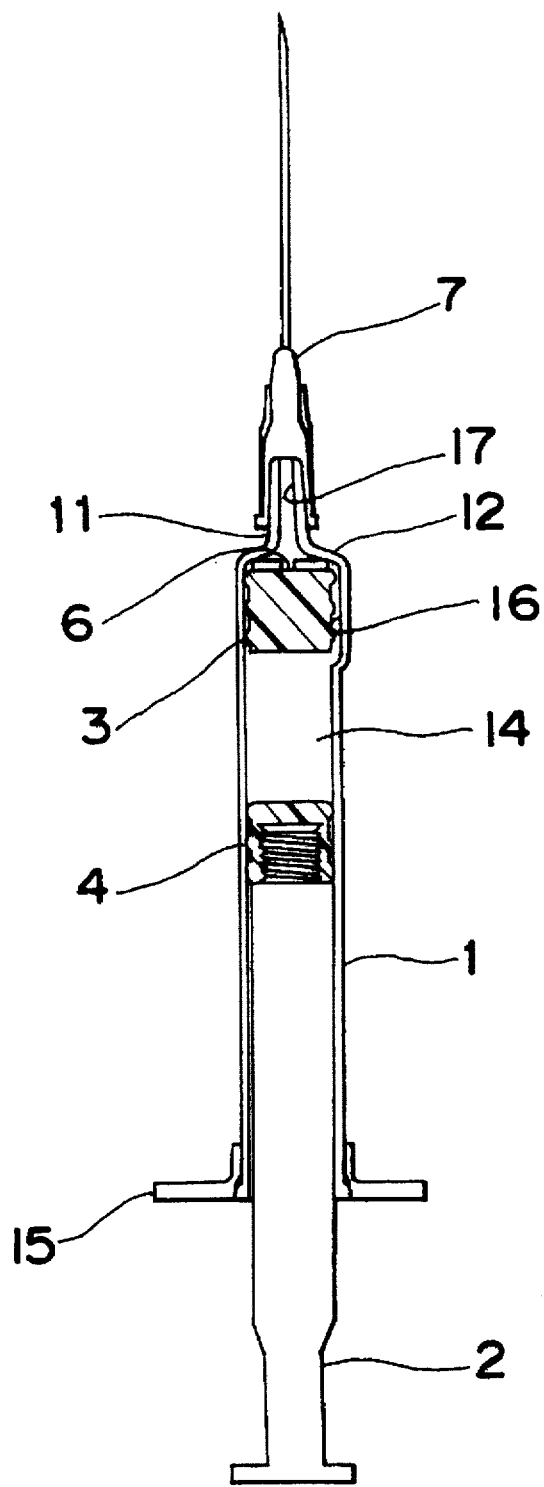
FIG. 3 is a cross-sectional view of the prefilled syringe just after a medical solution in the first chamber is pushed out through a needle which has been attached to the tip of the syringe after removal of a cap.

Referring now to FIGS. 1–3, the preferred embodiment of the present invention is shown as a prefilled syringe for injection of two liquid medicines, which comprises a syringe body 1 with a tip 11, the first and second gaskets 3, 4 liquid-tightly inserted in the syringe body 1 at certain intervals, a closing member or a cap 5 closing the tip 11 of the syringe body 1, and a plunger 2 adapted to force the gaskets 3, 4 to slide in the bore of the syringe body 1.

The syringe body 1 is composed of a cylindrical hollow member closed at one end but opened at the other end. The closed end of the syringe body 1 is provided with a tip 11 serving as an injection port. At the rear end or open end of the syringe body 1, there is provided a flange 15 for holding the syringe body 1 with fingers during operation. Further, the syringe body 1 is provided with a groove 16 extending from the inner wall of the closed end 12 in the longitudinal direction thereof to form a bypass between the injection port and the second fluid chamber 14 when the first gasket 3 is brought into contact with the inner wall of the closed end 12. The groove 16 is so designed as to have a length longer than the thickness of the first gasket 3 but shorter than the sum of the thickness of the first and second gaskets 3 and 4 to avoid blockage of the groove 16 by the first gasket 3 as well as to keep the sealing condition between the inner wall of the syringe body 1 and the second gasket 4 when the second gasket 4 is brought into contact with the first gasket 3.

Although the syringe body 1 may be made of a chemically resistant plastics such as polyethylene or polypropylene resins, it is generally made of glass in view of the fact that the prefilled syringe is preserved and transported under the conditions filled with medical solutions. However, it is difficult with glass to manufacture syringe bodies with a flange 15. Thus, the flange 15 may be made of plastics such as polyethylene or polypropylene resin separate from the syringe body 1 of glass and then attached to the syringe body 1.

The closed end 12 of the syringe body 1 may be provided with means for forming a passage between the closed end and the first gasket 3, i.e., a gap which makes liquid communication between the tip 11 and the bypass 16 when the first gasket 3 is brought into close contact with the inner wall of the closed end 12. This liquid communication means may be provided by forming one or more grooves or ribs on the inner wall of the closed end 12 of the syringe body 1. The liquid communication means may be provided on the front side of the first gasket 3 instead of the provision of the inner surface of the closed end 12 of the syringe body 1.

The first gasket 3 is a sealing member of elastic material which liquid-tightly fits into the bore of the syringe body 1 and is slidable along the inner wall of the syringe body 1, by which the space between the closed end 12 of the syringe body 1 and the second gasket 4 is partitioned into the first and second chambers 13, 14.

Figure 4:
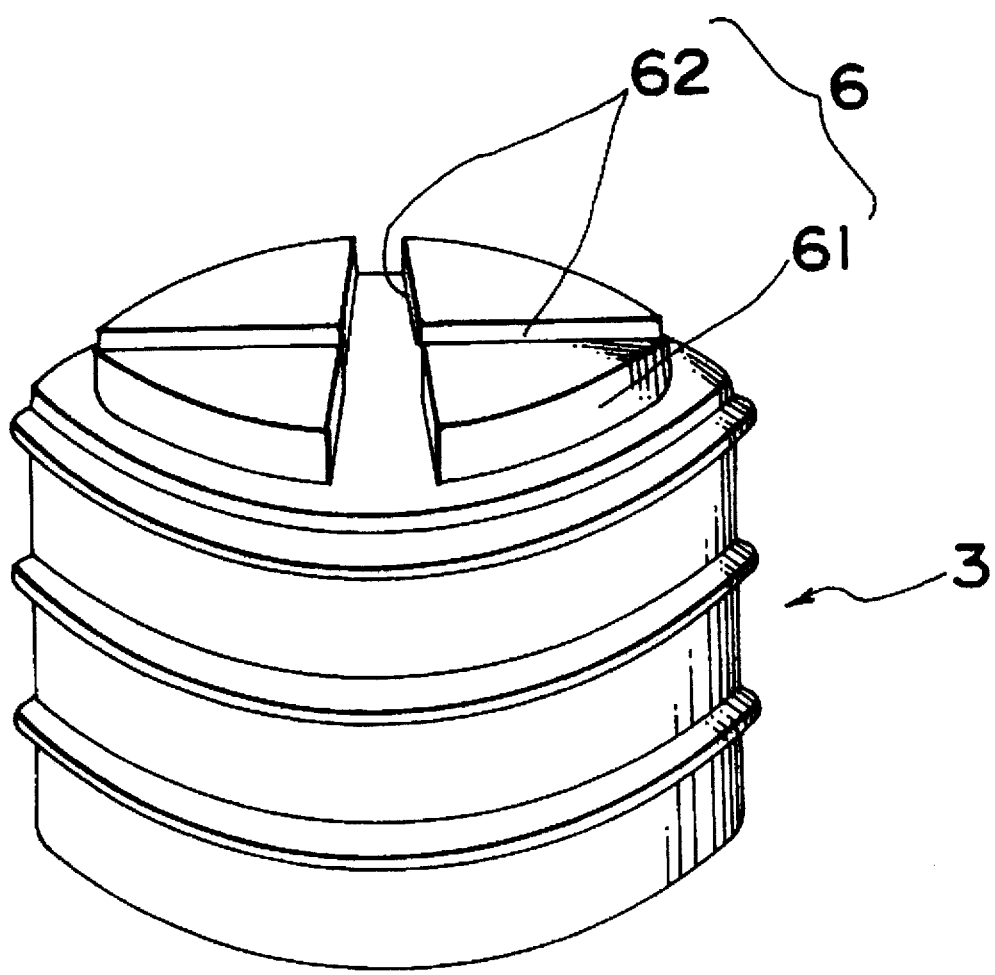
FIG. 4 is a perspective view illustrating one embodiment of the first gasket used in the prefilled syringe according to the present invention.

The liquid communication means for retaining a channel or passage for liquid is provided on the front surface of the first gasket 3 if the closed end 12 of the syringe body 1 is not provided with such liquid communication means. The liquid communication means may be constituted, for example, by providing grooves 6 in the front face of the first gasket 3, as shown in FIG. 4. The grooves 6 includes an annular groove 61 and crossed grooves 62 intersected each other at the center of the first gasket 3 and connected to the annular groove 61 at the peripheral portion of the first gasket 1.

Such liquid communication means may be formed by providing one or more projections or ribs on the front surface of the gasket 3 which are adapted to contact with the inner surface of the closed end 12 of the syringe body 1 so as not to close the lumen 17 of the tip 11. The liquid communication means shown in FIG. 4 may be regarded as being composed of four fan-shaped projections.

The second gasket 4 is a closing member of an elastic material which closes the open end of the syringe body and is slidable along the inner wall of the syringe body 1. Preferably, the front part of the second gasket 4 is covered with a film of a chemically resistant material such as polytetrafluoroethylene and the like. The second gasket is provided at its rear part with plunger attachment means 41 to which a plunger 2 is connected. In this embodiment, the plunger 2 is connected to the second gasket 4 by screw engagement, but this may be done by press-fitting or any other connecting means.

As can be seen from the above, the prefilled syringe 1 of the present invention has two chambers partitioned by the first gasket 3 as shown in FIG. 2. The first chamber 13 between the closed end 12 and the first gasket 3 is previously filled with a first medicine, for example, an anesthetic, while the second chamber 14 between the first and second gaskets 3, 4 is previously filled with a second liquid, for example, a high viscous medical solution. The plunger 2 is inserted in the syringe body 1 and fixed to the second gasket 4 by screw mounting.

In use, the cap 5 is removed first and then a needle 7 is fitted on the tip 11 of the syringe body 1. After this, two liquid solutions are injected under the skin one after another. During injection, the first and second gaskets 3, 4 are forced to move forward by pushing the plunger 2 into the syringe body 1 so that the anesthetic in the first chamber 13 is first administered to the site of the patient through the needle 7. When the first gasket 3 is brought into contact with the inner wall of the closed end 12 as shown in FIG. 3, the anesthetic in the first chamber 13 is pushed out completely. At the same time, the second chamber 14 is communicated with the injection port, i.e., tip 11, through the bypass or groove 16 and the liquid communication means 6. Thus, the second fluid in the second chamber 14 is pushed out through the bypass 16, liquid communication means 6 and the needle 7.

As can be seen from the above explanation, the use of the prefilled syringe of the present invention makes it possible to inject a medical solution without lowering narcotic influence when injecting a medical solution with a high viscosity, which in turn makes it possible to reduce a pain given to a patient.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A syringe for injection of two liquids comprising:
   a syringe body including a hollow tube having a closed end and an open end, said closed end including an injection port, said syringe body having at least one bypass groove extending from the closed end for a predetermined length along said syringe body;
   a first gasket being sealably fitted inside said hollow tube, said first gasket including at least two sector-shaped projections having at least one groove formed between said projections, said projections facing said closed end, said predetermined length of said bypass groove being substantially longer than a thickness of said first gasket;

a second gasket being sealably fitted inside said hollow tube, said first gasket being disposed between said closed end and said second gasket;

a first chamber within said hollow tube being filled with a first liquid, said first chamber being disposed between said first gasket and said closed end; and a second chamber within said hollow tube being filled with a second liquid, said second chamber being disposed between said first gasket and said second gasket, during injection the first fluid flows out of said injection port while said first gasket moves into said bypass groove, and when said first gasket contacts said closed end, the second fluid flows through said bypass groove and said at least one groove formed between said at least two-sector shaped projections and out of said injection port, whereby said first gasket substantially reduces mixing of said first and said second liquids.

2. The syringe according to claim 1, wherein said syringe body is made of at least one of polyethylene, polypropylene, and glass.

3. The syringe according to claim 1, wherein said first gasket is made of an elastic material.

4. The syringe according to claim 1, wherein said second gasket is made of an elastic material covered with a film of chemically resistant material.

5. The syringe according to claim 4, wherein said chemically resistant material is polytetrafluoroethylene.

6. The syringe according to claim 1, wherein said first gasket includes at least four sector-shaped projections with at least two intersecting grooves between said projections forming a cross-shape.

* * * * *